(12) United States Patent
Boccara et al.

(10) Patent No.: US 9,185,357 B2
(45) Date of Patent: Nov. 10, 2015

(54) OPTICAL TISSUE SECTIONING USING FULL FIELD OPTICAL COHERENCE TOMOGRAPHY

(75) Inventors: Albert Claude Boccara, Paris (FR); Fabrice Harms, Orsay (FR); Bertrand Le Conte Chrestien De Poly, Paris (FR)

(73) Assignee: LLTECH MANAGEMENT, Paris (FR)

( * ) Notice: Subject to any disclaimer, the term of this patent is extended or adjusted under 35 U.S.C. 154(b) by 262 days.

(21) Appl. No.: 13/822,852

(22) PCT Filed: Sep. 19, 2011

(86) PCT No.: PCT/EP2011/066246
§ 371 (c)(1),
(2), (4) Date: Mar. 13, 2013

(87) PCT Pub. No.: WO2012/035170
PCT Pub. Date: Mar. 22, 2012

(65) Prior Publication Data
US 2013/0182096 A1 Jul. 18, 2013

Related U.S. Application Data

(60) Provisional application No. 61/384,067, filed on Sep. 17, 2010.

(51) Int. Cl.
H04N 9/47 (2006.01)
H04N 7/18 (2006.01)
A61B 5/00 (2006.01)

(52) U.S. Cl.
CPC ............... *H04N 7/18* (2013.01); *A61B 5/0066* (2013.01); *A61B 5/0068* (2013.01)

(58) Field of Classification Search
None
See application file for complete search history.

(56) References Cited

U.S. PATENT DOCUMENTS 3,013,467 A * 12/1961 Minsky ................. 356/432
7,761,139 B2 * 7/2010 Tearney et al. ............ 600/473
(Continued)

FOREIGN PATENT DOCUMENTS

JP 2009264787 A * 11/2009
JP 2009264787 A * 11/2009

OTHER PUBLICATIONS

Denk W, Strickler J, Webb W (1990). "Two-photon laser scanning fluorescence microscopy". Science 248 (4951): 73-6).*
(Continued)

*Primary Examiner* — Jorge L Ortiz Criado
*Assistant Examiner* — Stefan Gadomski
(74) *Attorney, Agent, or Firm* — Osha Liang LLP (57) ABSTRACT

According to a first aspect, the invention relates to a multi-modal optical sectioning microscope (200, 400, 600) for full-field imaging of a volumic and scattering sample comprising: —a full-field OCT system for providing an image of a first section in depth of the sample comprising an illumination sub-system (201, 401, 601) and a full-field imaging interferometer with a detection sub system (208, 408, 608) and an optical conjugation device for optically conjugating the sample and said detection sub system, wherein said optical conjugation device comprises a microscope objective (203, 403, 603), —a supplementary full-field optical sectioning imaging system for providing a fluorescent image of a second section in depth of said sample comprising a structured illumination microscope with an illumination sub system (623), means (421, 422) for generating at the focal plane of said microscope objective of said full-field imaging interferometer a variable spatial pattern illumination and a detection sub system (624), optically conjugated with said focal plane of the microscope objective.

12 Claims, 6 Drawing Sheets

(56) References Cited

U.S. PATENT DOCUMENTS

| | | | |
|---|---|---|---|
| 7,872,759 B2* | 1/2011 | Tearney et al. | 356/479 |
| 8,115,934 B2* | 2/2012 | Boppart et al. | 356/479 |
| 8,983,580 B2* | 3/2015 | Boppart et al. | 600/473 |
| 2006/0158655 A1 | 7/2006 | Everett et al. | |
| 2007/0229801 A1 | 10/2007 | Tearney et al. | |

OTHER PUBLICATIONS

J. G. Fujimoto et al., Optical biopsy and imaging using optical coherence tomography, Nature Med. 1, 970-972 (1995).*

Jain M, Shukla N, Manzoor M, Nadolny S, Mukherjee S. Modified full-field optical coherence tomography: A novel tool for rapid histology of tissues. J Pathol Inform 2011;2:28.*

Ramanujam N., Fluorescence spectroscopy of neoplastic and non-neoplastic tissues, Neoplasia 2 (1-2), 89-117 (2000).*

International Search Report issued in PCT/EP2011/066246 mailed Jan. 23, 2012 (4 pages).

Written Opinion issued in PCT/EP2011/066246 mailed Jan. 23, 2012 (10 pages).

Arnaud Dubois et al.; "High-resolution full-field optical coherence tomography with a Linnik microscope"; Applied Optics, vol. 41, No. 4; pp. 805-812; Feb. 1, 2002 (8 pages).

Frederic Chasles et al.; "Optimization and characterization of a structured illumination microscope"; Optics Express; vol. 15, No. 24; pp. 16130-16140; Nov. 26, 2007 (11 pages).

Daryl Lim et al.; "Wide-field fluorescence sectioning with hybrid speckle and uniform-illumination microscopy"; Optics Letters; vol. 33, No. 16; pp. 1819-1821; Aug. 15, 2008 (3 pages).

Houssine Makhlouf et al.; "A dual modality fluorescence confocal and optical coherence tomography microendoscope"; Proceedings of SPIE vol. 7558; pp. 75580K-1-75580K-8; Jan. 24, 2010 (8 pages).

* cited by examiner

FIG.1

Prior Art

OPTICAL TISSUE SECTIONING USING FULL FIELD OPTICAL COHERENCE TOMOGRAPHY

BACKGROUND

The present invention is in the technical field of biomedical imaging, more particularly in the technical field of optical microscopy and more particularly in the technical field of optical sectioning microscopy.

Optical sectioning microscopy refers to the imaging of a section in depth of a sample, the section being in the focal plane of a microscope objective, while removing the background in the image due to out-of-focus light and scatter. When microscopy is applied to biological samples such as cells or tissues which exhibit strong scattering, optical sectioning dramatically improves the quality of the images obtained. It is thus of paramount importance for biological as well as medical purposes. Among the techniques that are used for high resolution imaging in the micrometer range, confocal microscopy (see for example U.S. Pat. No. 3,013,467—Minsky) and non-linear microcopies (e.g. two Photon—see for example Denk W, Strickler J, Webb W (1990). "Two-photon laser scanning fluorescence microscopy". Science 248 (4951): 73-6) are now widely used. They take advantage of large numerical aperture microscope (NA~0.8 to 1.4) objectives to achieve the required limited depth of field that insures good sectioning ability.

Optical Coherence Tomography (OCT) is an efficient optical sectioning technique for in-depth imaging of biological tissues. OCT relies on interferometric selection of ballistic photons (see for example J. G. Fujimoto et al., Optical biopsy and imaging using optical coherence tomography, Nature Med. 1, 970-972 (1995)). It has proved to be a highly valuable tool for biomedical imaging in particular in the field of eye examination. Concerning the other tissues of the human body that are dense and exhibit a very large scattering cross-section it is more difficult to get sharp images at the cellular level of virtual thin slices at large depths.

In contrast with most of the available OCT approaches (e.g. time domain OCT or Fourier domain OCT) Full Field OCT (FF-OCT) (see for example A. Dubois et al., High-resolution full-field optical coherence tomography with a Linnik microscope, Appl. Opt. 41, 805-812 (2002)) directly takes "en face" high resolution images (typically 1 µm, isotropic) using megapixels cameras coupled to gel or water immersion microscope objectives for a better matching of the refractive index of tissues.

Figure 1:
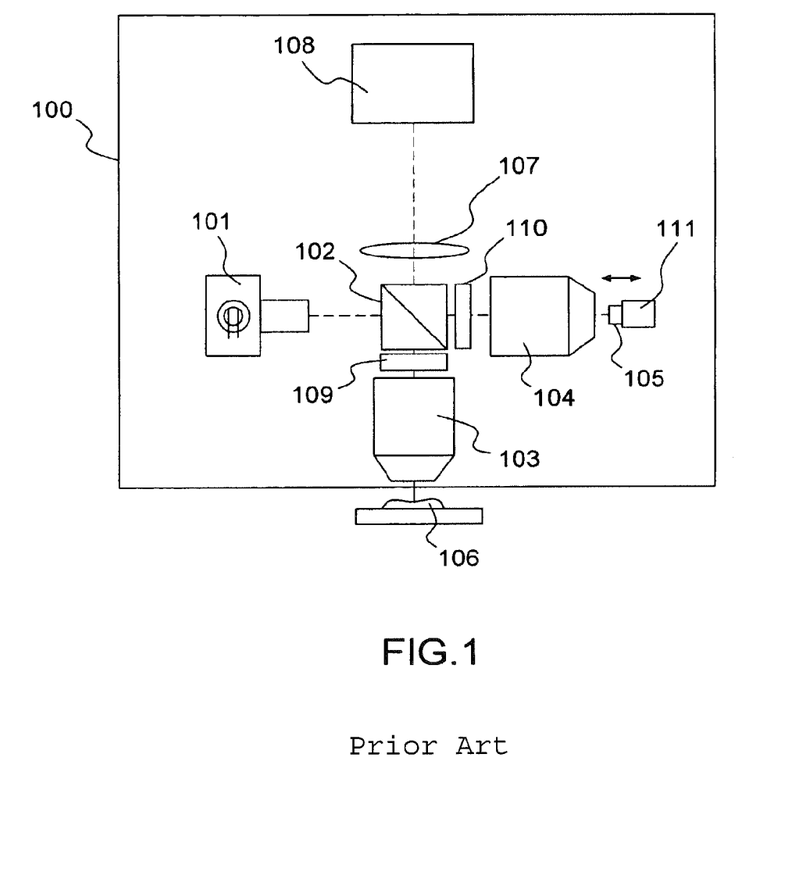
FIG. 1 shows an experimental setup for a full field OCT system according to the prior art (previously described)

The principle of a full-field OCT system is represented on FIG. 1. It relies on the use of thermal sources or arcs or LEDs that are spatially and temporally incoherent, coupled to an imaging interferometer, for example in the Linnik configuration as shown on FIG. 1. The FF-OCT system 100 comprises a source of partially coherent light 101, e.g. an halogen light source, optically integrated in a Köhler illuminator so as to provide uniform illumination in the sample, a beamsplitter 102, e.g. a non-polarizing beamsplitter cube, defining two interferometric arms. For a Linnik configuration, both arms include a microscope objective of the same characteristics 103 and 104. In one arm, further named the reference arm, a uniform reflective surface 105 is positioned at the focal plane of the objective and linked to an oscillator 111, allowing modulation of the optical path length of the reference arm, e.g. a piezo electric transducer. In the other arm, further called object arm, a volume and scattering sample 106—to be imaged—is positioned at the focal plane of the objective 103. An adjustable dispersion balance system is included in both arms, e.g. rotating glass plates 109 and 110. A tube lens 107 is placed at the output of the interferometer in order to conjugate the focal planes of both objectives 103 and 104 with a multichannel detector 108, e.g. a CCD or CMOS matrix. The magnification of the imaging interferometer is fixed, defined by the focal characteristics of the microscope objective 103 and tube lens 107. The adjustment in depth of the device 100 relative to the sample 106 is performed using translation means, e.g. a motorized linear translation stage.

Due to the broad spectrum of the source, interferences occur only when the optical path lengths of the two arms of the interferometer are identical within typically 1 µm. Moreover the spatial incoherence of the source prevents cross talk between pixels. The signal is extracted from the background of incoherent backscattered light using a phase-shifting method. Due to the randomness of the tissues structures, it is possible to record only two interferometric images, using a CCD or a CMOS camera for example, the phase being changed by $\pi$ in the interferometer reference channel between each image and to compute the tomographic image by calculating the normalized difference of the interferometric images.

The FF-OCT system—or at least part of its components—can be displaced to move the focal plane at different depths within the sample in order to obtain 2D images at different depths that can be further reconstructed into 3D images, which we will call 3D tomographic images. En face capture allows the FF-OCT system to operate with high lateral resolution (typically ~1 µm) using medium aperture microscope objectives (for instance, but not limited to 10× or 20× water immersion objectives with 0.3 to 0.5 numerical aperture). In addition, micrometric displacement of the FF-OCT system will enable 3D tomographic images at a 1 micron or less vertical resolution.

FF-OCT allows for ultra high resolution (typically ~1 µm in 3D) images of scattering samples such as biological tissues, in depth, using a non-invasive process. Typical morphologic structures of tissue show sizes starting from a few microns to a few tens of microns. For example the size of a cell nucleus is typically between 5 and 10 µm, the size of a typical adipose cell between 25 and 50 µm. Due to its high resolution capabilities, the FF-OCT technique is able to provide cellular resolution images of morphologic characteristics of tissues, compared to conventional OCT techniques such as Time-Domain OCT or Fourier-Domain OCT, which have a limited transverse resolution of about 10 µm, preventing from resolving fine cellular structures. It has been proven that the use of the FF-OCT on various tissues is of great interest for pathologists (see "Jain M, Shukla N, Manzoor M, Nadolny S, Mukherjee S. Modified full-field optical coherence tomography: A novel tool for rapid histology of tissues. J Pathol Inform 2011; 2:28"), as a new tool for fast, non-invasive, non-sacrificial assessment method on freshly excised tissue. Applications such as biobanking, embryology, or surgery guidance have been raised by pathologists. For example FF-OCT might be used in the future for evaluation of surgical margins, or as a confirmation tool for assessing the adequacy of biopsied tissue for subsequent definitive histo-pathological diagnoses. The main advantage is that, for some clinical situations, the technique can provide significant pathological and architectural information within minutes, without the need to prepare histology slides, which a time-consuming, operator-dependant process.

However, compared to histology slides, which are the "Gold Standard" in pathology, the information given by standard FF-OCT images is mainly limited to morphology and architecture. Indeed, the contrast provided by FF-OCT results from the local variation of the amount of ballistic photons due to local refractive index variations linked to tissue structures. The contrast risen by the FF-OCT technique on particular metabolic structures such as tumorous areas of a tissue, is not always enough to perform an accurate diagnostic. In standard histology, pathological areas are often revealed using chemical coloration, such as H&E staining (Hematoxylin and Eosin). After coloration and histology slide preparation, cancerous tissue usually appears in a different color compared to the surrounding healthy tissue, with sharp contrast based on coloration. Moreover, such a contrast can be used at high magnification on a microscope to observe fine cellular structures such as cell nuclei. The size and density of nuclei is often considered as a good indicator of cancerous invasion, the size of the nuclei of cancerous cell being larger than the nuclei of healthy cells. As a consequence, when using FF-OCT microscopy on biological tissues, it may be useful for pathologists to enhance the contrast of specific cellular structures, such as cell nuclei or cancerous tissue areas. Such an additional contrast can provide both morphologic and metabolic information in a single image, approaching the information given by standard histology slides.

In standard microscopy, this additional contrast can be obtained using coloration fluids in histopathology, or fluorescent agents such as GFP (Green Fluorescent Protein) in biology. For example fluorescence spectroscopy has been used to detect early dysplasia in various organs (see Ramanujam N., Fluorescence spectroscopy of neoplastic and non-neoplastic tissues, Neoplasia 2 (1-2), 89-117 (2000)). The principle of fluorescence microscopy relies on the addition of a fluorescent agent to the sample—sometimes with specificity to a cellular structure—followed by the illumination of the sample using light with a spectrum corresponding to the absorption spectrum of said fluorescent agent. The subsequent fluorescence emission is characterized by a shifted spectrum compared to the absorption spectrum, usually towards higher wavelengths.

In conventional fluorescence microscopy of biological objects, the illumination light passes through a volume of the sample, so that the emission of fluorescence also occurs at out of focus planes. The resulting image is then blurred by a fluorescent background noise. As a consequence, fluorescence microscopy is usually used in combination with an optical sectioning technique, which allows for collecting light only coming from the sectioning plane, thus removing out of focus fluorescent noise.

However, OCT techniques, including the FF-OCT technique, are not compatible with fluorescence microscopy as light coming from the emission of fluorescence of the sample is incoherent with the light source. The properties of fluorescent photons are not correlated to the properties of the low-coherence source used for coherence tomography. Consequently, the optical path length equalization between the two interferometric arms is not possible anymore, and interference signals necessary to coherence tomography techniques can not be obtained.

One objective of the present invention is to provide additional contrast(s) in an FF-OCT system.

SUMMARY OF THE INVENTION

According to a first aspect, the present disclosure relates to a multimodal optical sectioning microscope for full-field imaging of a volumic and scattering sample comprising:
a full-field OCT system for providing an image of a first section in depth of the sample comprising an illumination sub-system and a full-field imaging interferometer with a detection sub system and an optical conjugation device for optically conjugating the sample and said detection sub system, wherein said optical conjugation device comprises a microscope objective,
a supplementary full-field optical sectioning imaging system for providing a fluorescent image of a second section in depth of said sample comprising a structured illumination microscope with an illumination sub system, means for generating at the focal plane of said microscope objective of said full-field imaging interferometer a variable spatial pattern illumination and a detection sub system, optically conjugated with said focal plane of the microscope objective.

In the multimodal optical sectioning microscope of the first aspect, the full-field OCT system and the supplementary full-field optical sectioning imaging system are combined to share at least partially a common optical imaging channel. It is thus possible to provide additional contrasts in an FF-OCT system while keeping a compact apparatus implementing a parallel detection of each point of the image. Further, sharing the same microscope objective enables providing images of the same zone of the sample, with the same transversal resolution and different contrasts.

According to an embodiment, the supplementary full-field optical sectioning imaging system and the FF-OCT system have the same illumination sub-system and/or detection sub-system.

According to another embodiment, the supplementary full-field optical sectioning imaging system and the FF-OCT system have different illumination sub-system and/or detection sub-system. Typically, the useful illumination bandwidth for a FF-OCT system is in the near infrared (600-900 nm) as a good compromise between penetration depth in biological samples and optical resolution, whereas the excitation/emission spectra of a lot of fluorophores is in the range 350-600 nm. When using for the full-field OCT system and the full-field optical sectioning system different illumination sub-system and/or detection sub-system, it will be very easy to combine and/or separate the respective light beams in both systems using dichroic beamsplitters.

According to a preferred embodiment, the spatial pattern is substantially periodic. According to further embodiments, the spatial pattern may be a speckle, or a combination of varying speckles, or a random transmission pattern.

According to a preferred embodiment, the means for generating the spatial pattern comprise a mask with variable spatial transmittance or reflectance to be illuminated by the illumination sub-system of said supplementary full-field optical sectioning imaging system and conjugated with the focal plane of said microscope objective.

According to another embodiment, the illumination sub-system of said supplementary full-field optical sectioning imaging system is a laser and said means for generating the spatial pattern comprise a diffuser to be illuminated by said laser and conjugated with the back aperture of said microscope objective.

According to a preferred embodiment, said full-field imaging interferometer further comprises a beamsplitter defining a reference arm with a reference mirror and an object arm for receiving the sample and comprising said objective microscope.

According to a second aspect, the present disclosure relates to a method of acquiring in depth section images of a volumic and scattering sample using a FF-OCT system and in depth section fluorescent images using a supplementary full-field optical sectioning imaging system, wherein said FF-OCT system and said supplementary full-field optical sectioning imaging system share a common optical channel.

According to a preferred embodiment,
acquiring images of said first section of the sample comprises optically conjugating said sample with a detection sub-system of a full-field imaging interferometer using a microscope objective, and
acquiring fluorescence images of said second section of the sample comprises generating at the focal plane of said microscope objective of said full-field imaging interferometer a variable spatial pattern illumination, forming a plurality of images for different spatial pattern illumination on a detection sub-system optically conjugated with the focal plane of said microscope objective and processing said plurality of images to obtain said fluorescence images.

According to an embodiment, said method comprises simultaneous acquisition of images from said supplementary full-field optical sectioning imaging system and said FF-OCT system.

According to an embodiment, simultaneous acquisition is obtained using spectral separation of light used for each imaging channel of said supplementary full-field optical sectioning imaging system and said FF-OCT system.

According to an embodiment, simultaneous acquisition is obtained using a multispectral array detector common for said supplementary full-field optical sectioning imaging system and said FF-OCT system.

According to an embodiment, simultaneous acquisition is obtained using a single detector and the discrimination of data coming from said supplementary full-field optical sectioning imaging system and said FF-OCT system is performed using post processing of data acquired by the single detector.

According to a further embodiment, said method further comprises displaying said first and second fluorescent images, and displaying merged images from said first and second fluorescent images.

DETAILED DESCRIPTION OF A PREFERRED EMBODIMENT

Figure 2:
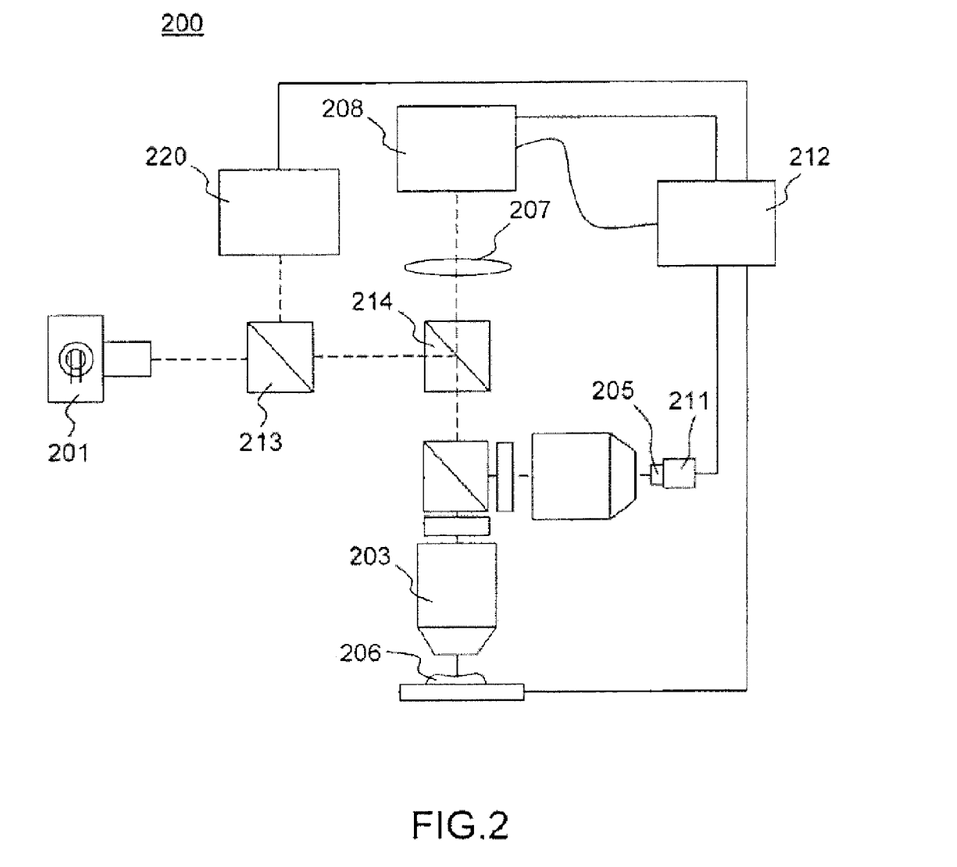
FIG. 2 shows a sub-system representation of an experimental setup for a multimodal Full-Field OCT system according to the present invention.

FIG. 2 shows an example of a multimodal FF-OCT system according to the present disclosure.

The system comprises a FF-OCT system as described for example in FIG. 1 with an illumination sub-system 201, a full-field imaging interferometer to take en face 3D tomographic images of a sample 206 and a processing sub-system 212. The illumination sub-system 201, for example an halogen lamp, emits a first incident wave having a low temporal coherence. The sample 206 is for example a volume and scattering medium such as a biological tissue. The imaging interferometer comprises an interferometric sub-system (as it will be detailed in reference to FIGS. 3A to 3B) and a detection sub-system 208, for example a CCD or CMOS camera at the focal plane of a tube lens 207. The interferometric sub-system comprises a reference arm with a reference mirror 205, an object arm for receiving the sample 206 and means for varying the relative path difference between the object and reference arms, for example an oscillator 211, e.g. a piezo electric transducer. The object arm comprises a microscope objective 203. An optical conjugation device comprising in the example of FIG. 2 the microscope objective 203 and the tube lens 207 optically conjugates the sample and detection subsystem 208. The imaging interferometer allows for the acquisition of at least one first and one second interferometric images resulting from the interference of a reference wave obtained by reflection of said first incident wave on said reference mirror and an object wave obtained by backscattering of said first incident wave by a first section of the sample at a given depth of the sample, the at least two interferometric images having a phase difference obtained by varying the relative path difference between the object and reference arms. The processing sub-system 212 processes said interferometric images to obtain a tomographic image of said first section of the sample, whose depth is equal to the coherence length of the source divided by the double of the refractive index of the immersion medium.

The multimodal FF-OCT system further comprises a supplementary full-field optical sectioning imaging system 220, 203 linked to the processing sub-system 212 for providing a fluorescent image of the sample 206, and optical coupling means 213, 214 for optically coupling an imaging channel of the supplementary imaging system with the object arm of the imaging interferometer. The imaging channel of the supplementary full-field optical sectioning system comprises the microscope objective 203 of the object arm of the interferometric sub-system. The supplementary imaging system may comprise its own illumination and detection sub-systems or use the same illumination and/or detection sub-systems as those of the FF-OCT system. Different configurations of the supplementary imaging system 220 will be described later.

Information coming from the detection sub-system 208 and the supplementary imaging module 220 are collected and processed by the processing sub-system 212. The processing sub-system 212 is typically a computer, and processing includes typically collecting, processing and displaying data. It further includes synchronization and control of the different sub-systems, as for example vertical movement of the sample 206, switching ON/OFF of the illumination sub-systems, control of the optical path length difference of the interferometric sub-system.

The FF-OCT system and supplementary full-field imaging system share an at least partially common optical channel, which makes it possible to build a cost-effective, small footprint multimodal optical sectioning imaging system.

Figure 3A:
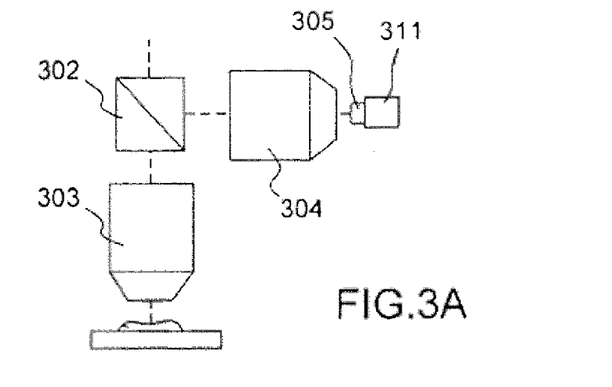
FIG. 3A to 3C show different embodiments for a full-field interferomer.
Figure 3B:
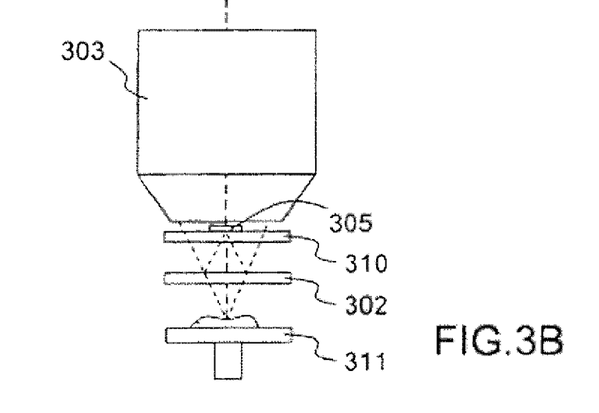
Figure 3C:
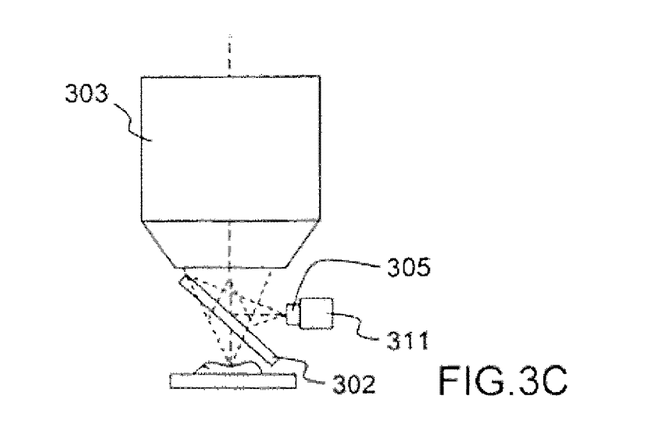

FIGS. 3A, 3B and 3C illustrate 3 examples of interferometric sub-systems. FIG. 3A describes a Linnik type interferometric sub-system as shown on FIG. 2, comprising a beamsplitter 302, for example a non-polarizing broadband beamsplitter cube, microscope objectives 303 and 304 having the same optical characteristics, for example ×10 NA 0.3 water immersion objectives, an homogeneous reflective surface 305, an oscillator 311 allowing modulation of the optical path length of the reference arm, e.g. a piezo electric transducer. This configuration is equivalent to the basic configuration of a FFOCT microscope as previously described in FIG. 1. FIG. 3B shows an alternative interferometric sub-system, based on a Mirau configuration. It comprises a microscope objective 303 having moderate magnification and numerical aperture, e.g. ×10 and 0.3, a beamsplitter 302 such as a non-polarizing 50:50 beamsplitter, an optical window 310 having the same optical characteristics as 302 in terms of dispersion and optical path length, for example a transparent plate of the same material and thickness as 302, and an homogeneous reflective surface 305 positioned at the focal length of the objective 303. The beamsplitter 302 defines the 2 interferometric arms of the interferometric sub-system. The modulation of the optical path length is ensured using an oscillator 311, for example a piezoelectric transducer. FIG. 3C shows another interferometric sub-system based on a Michelson configuration. It comprises a microscope objective 303 having moderate magnification and numerical aperture, e.g. ×10 and 0.3, a beamsplitter 302 such as a pellicle beamsplitter, an homogeneous reflective surface 305 positioned at the focal length of the objective 303. The beamsplitter 302 defines 2 interferometric arms of the interferometric sub-system. As for the Linnik of Mirau configuration, the modulation of the optical path length is ensured using an oscillator 311, for example a piezoelectric transducer.

According to a preferred embodiment, the supplementary full-field optical sectioning imaging system comprises a structured illumination microscope, which in addition to be a Full-field imaging technique and showing a sectioning ability, is compatible with fluorescence imaging.

A basic principle of Structured Illumination Microscopy (SIM) according to a first variant is described for example in Juskaitis, R., Wilson, T., Neil, M. A. A. and Kozubek, M. "Efficient real-time confocal microscopy with white light sources" (Nature 383: 804-806 (1996)), and optimization as well as design considerations can be found in Chasles, F., Dubertret, B. and Boccara, A. C. "Optimization and characterization of a structured illumination microscope" (Optics Express 15: 16130-16140 (2007)).

Basically, according to this variant, SIM is based on the modulation of the intensity of illumination light at the imaging plane using a periodic structure, typically a 1 dimensional grid with a contrast of 1, thus forming a variable periodic spatial pattern. The grid is projected on the sample using relay optics, and transversally modulated usually using a piezoelectric transducer. The modulation is performed by shifting the grid by at least three steps of equal amplitude along a grid period. If I1, I2 and I3 are the three recorded intensity images using a square pattern grid, the demodulation is performed using the following formula:

$$S = \sqrt{[(I1-I2)^2 + (I1-I3)^2 + (I2-I3)^2]}$$

When using a sinusoidal pattern grid, 4 images over a sinusoid period are used to retrieve the sectioned imaging plane. The demodulation formula becomes (see Chasles, F., Dubertret, B. and Boccara, A. C. "Optimization and characterization of a structured illumination microscope". Optics Express 15: 16130-16140 (2007)):

$$S = \sqrt{[(I0-I1)^2 + (I2-I3)^2]}$$

Where I0, I1, I2, I3 are respectively the 4 recorded intensity images. The use of a sinusoidal pattern is particularly efficient in suppressing residual modulation artifacts that sometimes arise from the use of the structured illumination technique. The movement of the spatial pattern, depending on the detection principle, can be either stepwise or substantially continuous.

The result is representative of an optical section which characteristics in thickness are linked to the period of the grid in combination with the numerical aperture of the microscope objective. The optimum resolution is obtained with a period substantially equal to the resolution limit of the imaging optics, usually a microscope objective.

Figure 4:
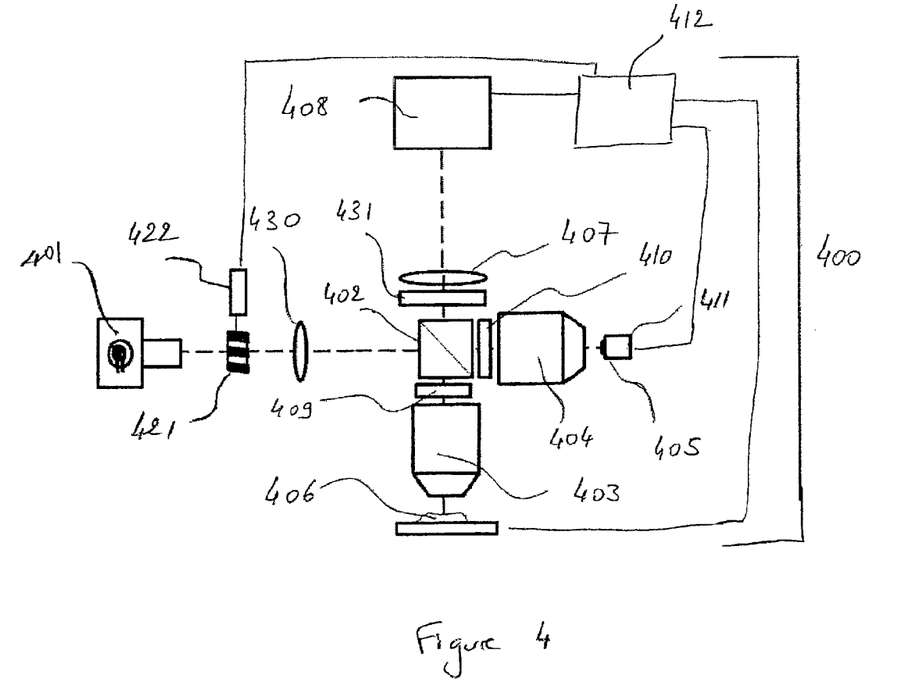
FIG. 4 shows an experimental system according to a first embodiment of a multimodal FF-OCT system according to the present invention.

FIG. 4 shows an experimental system according to a first embodiment of a multimodal FF-OCT system according to the present disclosure incorporating a structured illumination microscope. The system 400 is a Full-Field Optical Coherence Tomography microscope including an additional sectioning capability for providing both a tomographic image and a fluorescent image of a sample.

The microscope 400 comprises a source 401 which is spatially and temporally low coherent, typically a halogen or xenon lamp or a LED or combination of LEDS, and an imaging interferometer comprising a beamsplitter 402, typically a non-polarizing beamsplitter cube, defining two interferometric arms. Both arms include a microscope objective 403 and 404 of the same characteristics. In one arm, further named the reference arm, a uniform reflective surface 405 is positioned at the focal plane of the objective and linked to an oscillator 411, allowing modulation of the optical path length of the reference arm, e.g. a piezo electric transducer. In the other arm, further called object arm, the volume and scattering sample 406 is positioned at the focal plane of the objective 403. An adjustable dispersion balance system is included in both arms, e.g. rotating glass plates 409 and 410. Glass plates 409 and 410 also exhibit an optimized transmission ration in order to optimize the interference contrast. A tube lens 407 is placed at the output of the interferometer in order to conjugate the focal planes of both objectives with a multichannel detector 408, e.g. a CCD or CMOS matrix. The magnification of the imaging interferometer is fixed, defined by the focal characteristics of the microscope objective and tube lens. The adjustment in depth of the device 400 relative to the sample 406 is performed using translation means, e.g. a motorized linear translation stage.

The system further comprises a mask 421 with variable spatial transmittance along one axis, e.g. a grid, positioned in this embodiment along the illumination path, preferably in the plane of the field stop or conjugated with the plane of the field stop of the imaging interferometer. The profile of the variable spatial transmittance is preferably chosen as sinusoidal intensity modulation, but can also exhibit a square modulation pattern. The lens 430 conjugates the grid through the objective 403 with the focal plane of the objective 403, so that the sample 406 is illuminated with the corresponding modulated pattern. Variable spatial transmittance masks are typically obtained using microlithography on glass substrates. Alternative methods might be chosen to provide the spatially modulated illumination pattern, such as a liquid-crystal spatial light modulator, or digital micro mirror (DMD), or any other system exhibiting variable spatial transmittance capabilities. A modulator 422 is physically linked to the mask 421 in order to perform the minimum 3-step translation of the mask 421 required in the structured illumination microscopy process previously described. According to a preferred embodiment, a filter 431, typically a long pass filter is positioned along the imaging path in order to isolate a specific spectrum of the collected light.

Advantageously, the optical filter 431 is advantageously chosen as to filter out the excitation fluorescence wavelengths, without removing any FFOCT and fluorescence information. For example the excitation spectrum of a lot of fluorophores includes blue wavelengths around 400 nm, whereas the emission spectrum is often in the orange to red wavelengths starting around 500 nm, just before the typical bandwidth of FFOCT begins.

In the embodiment as described on FIG. 4, the two imaging modules (FF-OCT and SIM) share the optical microscope composed of the objective 403, the glass plate 409, the beamsplitter 402, the filter 431, the tube lens 407 and the detector 408. This common optical subsystem exhibits several advantages regarding the combination of the two modules. In particular, the sampling of the image by the detector is the same for both modules, so that FFOCT and SIM images are automatically co-registered. Further, the common use of the objective 403 allows for obtaining the same transverse resolution for both modules. As a consequence, the comparison and/or merging of images given by the two techniques does not require any image modification, re-sampling or post-processing.

In the embodiment as described on FIG. 4, it is possible to acquire images from both techniques simultaneously, which results in an advantageous capability of merging the images coming from both modules even in the case of time varying samples such as in vivo biological specimens.

Figure 5:
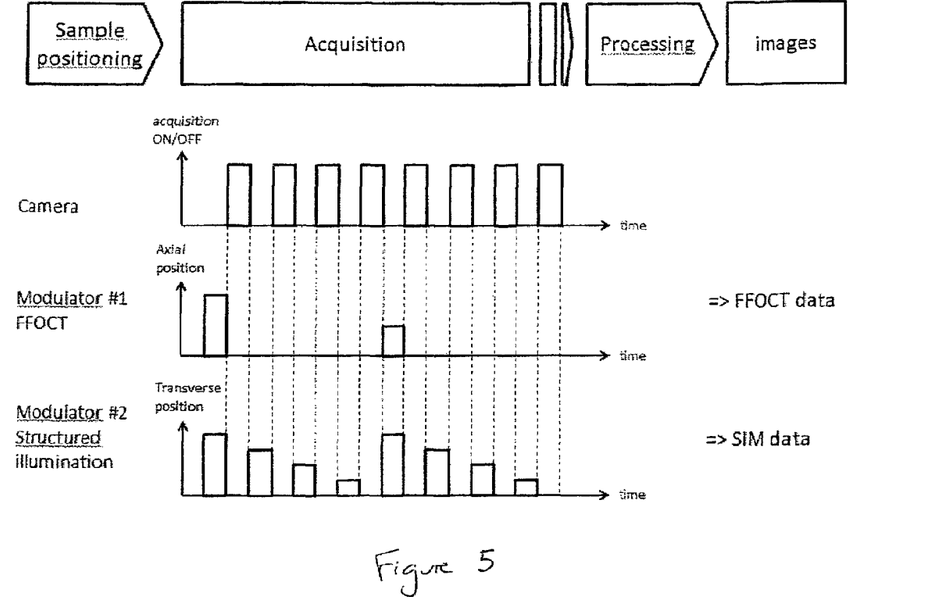
FIG. 5 shows a diagram describing the acquisition procedure of an experimental system according to the multimodal FF-OCT system according to FIG. 4.

FIG. 5 shows an example of a data acquisition cycle using the system as described in FIG. 4. After positioning of the sample, a processing unit 412 including synchronization capabilities, such as a dedicated I/O board linked to computer, is used to generate trigger signals to the array detector 408, e.g. a camera, and to the oscillators 411 and 422. As previously explained, the FFOCT technique requires 2 images with a phase shift in between, whereas the SIM technique usually requires 4 images with a spatial shift of the grid in between. In the acquisition process as shown on FIG. 5, a first image is acquired with the first position of the FF-OCT oscillator and a first position of the SIM oscillator. Then 3 other images are acquired for three other positions of the SIM oscillator. This scheme is repeated once after a shift of the FFOCT oscillator. The result is an acquisition of 8 images, available for post processing and display.

If I(x,y) is the intensity in the transverse plane of the image, then, using a sinusoidal grid as a SIM modulator:

$I0 = I \cdot \sin(wx)$, w being the spatial frequency of the grid along the x axis, is the corresponding modulated intensity for a first position of the grid. The three other images corresponding to the three additional shifted positions of the grid are:

$$I1 = I \cdot \sin(wx + \pi/2)$$

$$I2 = I \cdot \sin(wx + \pi)$$

$$I3 = I \cdot \sin(wx + 3\pi/2)$$

As previously described the SIM sectioning image is given by:

$$S = \sqrt{[(I0-I1)^2 + (I2-I3)^2]}$$

In that case, it is possible to use such a modulated signal to advantageously retrieve the demodulated image in order to perform the FFOCT processing. Indeed the original non modulated image can be calculated following:

$$I = \tfrac{1}{2}\sqrt{(I0^2 + I1^2 + I2^2 + I3^2)}$$

As a consequence, with a set of 8 images acquired regarding the synchronization diagram presented in FIG. 5, it is possible to retrieve both FFOCT and SIM images corresponding to the acquisition time of these 8 initial images.

Such a synergy between the two techniques induces several advantages. In particular, an automatic coregistration of images can be performed thanks to the use of a single detector. Further, the adaptation of the initial FF-OCT system is limited to the insertion of the spatial modulation in the illumination path and a filter, which is very simple to realize as phase shifting algorithms are very similar between FFOCT and SIM.

Figure 6:
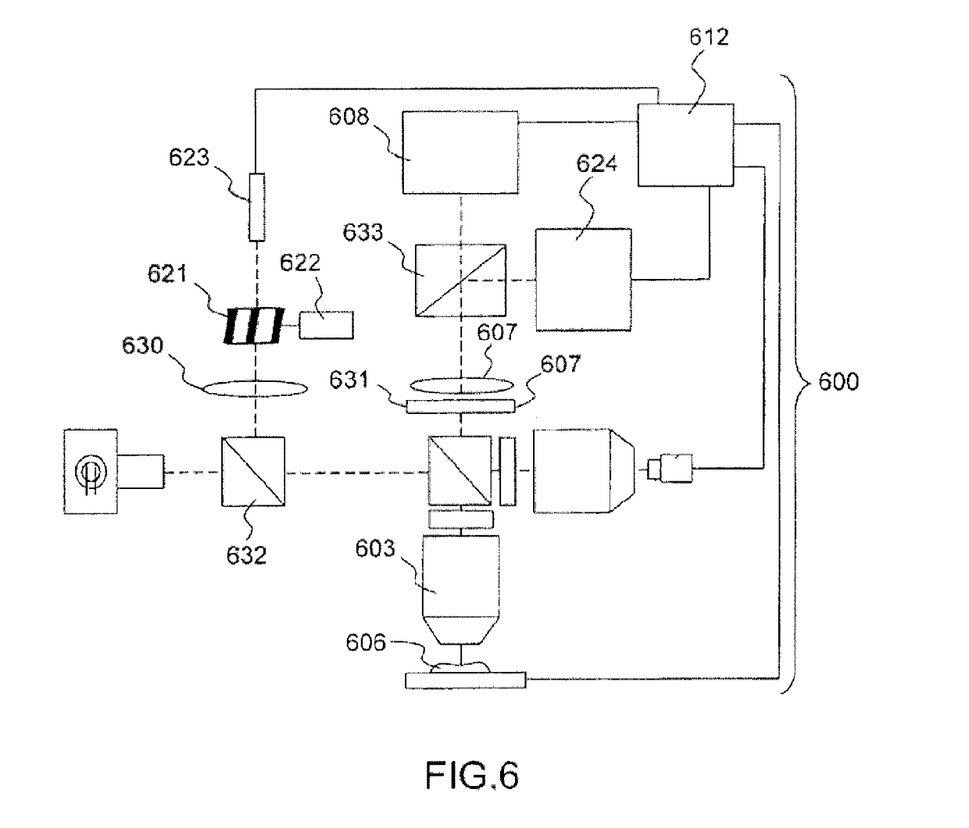
FIG. 6 shows an experimental system according to a second embodiment of a FF-OCT system according to the present invention.

FIG. 6 shows an experimental system according to a second embodiment of a multimodal FF-OCT system incorporating a structure illumination module. The system is similar to the system of FIG. 4 except for the illumination subsystem and detection sub system. In the case of fluorescence imaging using SIM, the detected photons are the fluorescence photons added to the FFOCT photons. For optimizing the sensitivity of both techniques, it may be advantageous to separate the two imaging channel at the illumination and detection levels. In this way, one—or more—source 623 of optimal characteristics for fluorescence excitation, for example with a spectrum corresponding to the excitation spectrum of the fluorescent dye used, is used to illuminate the sample 606 through a mask 621 of variable spatial transmittance, e.g a grid, modulated by the oscillator 622, as already described in FIG. 4. The grid 621 is conjugated with the sample imaging plane using optics 630 and 603, and this SIM illuminator is inserted into the common path using a beamsplitter 632, for example a dichroic non-polarizing beamsplitter cube starting transmitting light at 600 nm, in order to efficiently combine sillumination spectra from both modalities. A dedicated multichannel detector such as a low noise CCD or CMOS camera 624 is inserted in the detection subsystem using a beamsplitter 633 such as a dichroic non-polarizing cube beamsplitter, allowing to advantageously direct fluorescent photons only to the detector 624 and to direct tagged FFOCT photons only to the detector 608, if the fluorescence spectrum is chosen to be significantly separated from the FFOCT spectrum. Also a filter 631, typically a long-pass filter, is inserted before the tube lens 607 in order to avoid detecting light corresponding to the fluorescence excitation spectrum, which is usually lower than the emission spectrum, with a typical cut-off wavelength of 450 nm. Typically the dichroic beamsplitter reflects wavelengths under 600 nm and transmits wavelengths over 600 nm. The other components of the system 600 are similar to the components described in FIG. 4. This configuration optimizes the sensitivity of both techniques, as the fluorescence signal is usually very weak, requiring the use of a high-sensitivity detector. In this embodiment, as spectral separation of the beams from the different modalities is performed, it is also possible to acquire signals from the different modalities simultaneously, using a dedicated synchronization scheme implemented by the processing unit 612. Alternatively, a multispectral camera can be used for spectral discrimination of data, for example JAI model AD-O80-GE which includes 2CCD chips with bandwidths of 400-700 nm (used for SIM) and 700-900 nm (used for FFOCT).

Alternative full-field optical sectioning techniques can also be advantageously used in combination with FFOCT, including dynamic speckle illumination, HiLo microscopy, aperture correlation microscopy. These techniques also exhibit full-field optical sectioning, and all comprise structured illumination microscopy. But contrary to the so called "SIM" previously described, the variable spatial pattern illumination is no longer necessarily periodic, as it will be described in details below. These techniques can advantageously be used for background reduction in fluorescence imaging.

Dynamic Speckle Illumination (DSI) is a structured illumination technique which consists in illuminating the imaging plane in depth in the sample using a random speckle pattern, dynamically changing the speckle pattern projected, and computing a series of obtained images to retrieve an optical section in depth of a scattering sample. The technique has been introduced in C. Ventalon et al., Quasi-confocal fluorescence sectioning with dynamic speckle illumination, Optics Letters vol. 30 no 24, 3350-52, 2005. Dynamic speckle illumination is typically achieved by the use of a laser source and a rotating diffuser or spatial light modulator. The diffuser creates a random speckle pattern for each of its position, and is conjugated with the back aperture of the objective. A number of images, typically between 50 and 100 are acquired and the rms or the variance of each pixel of a detector, typically a 2D camera, over the series of images is computed to produce a full-field optical section of a sample. As described by the previous pioneering paper, the technique is applicable to fluorescence imaging.

HiLo microscopy has been first introduced in D. Lim et al., Wide-field fluorescence sectioning with hybrid speckle and uniform illumination microscopy, Optics Letters vol. 33 no 16, 1819-21, 2008. This technique is an evolution of DSI, allowing for the use of only 2 images to compute a full-field optical section of a sample in depth. First, as for DSI, the use of a laser source and a diffuser allows for speckle projection in the sample, and a corresponding image is acquired using a 2D detector, typically a CCD or CMOS camera. Then the diffuser is rotated in order to average speckle, so that a uniform illumination is projected in the sample, and a corresponding image is acquired by the detector. The first image is used to retrieve in-focus low spatial frequencies typically using low-pass filtering, such as the computation of the ratio between the variance and the mean on a mosaic of areas of a few pixels, over the whole image. The second image is used to retrieve high spatial frequencies, typically using high-pass filtering, such as the use of dedicated filter in the Fourier space, after fast Fourier transform on the initial image. The normalized sum of the two computed image corresponds to an optical section of the sample over all spatial frequencies. The technique is also applicable to fluorescence imaging.

Aperture correlation microscopy has been first introduced in T. Wilson et al., "confocal microscopy by aperture correlation", Optics Letters vol. 21 no 23, 1879-81, 1996. As for conventional structured illumination microscopy, it relies on the use of structured light projected on the sample. In this evolution of SIM, the mask used for creating the modulation pattern is typically exhibits a random transmission pattern in one sector, and a blank sector. The mask is rotated during the acquisition of the camera, mimicking the principle of a spinning-disk microscope, and two images are acquired, one containing modulated light from the random pattern sector of the mask as well as out-of-focus light, and one standard widefield image from the blank sector. The random pattern ensures zero cross correlation between pixels. A scaled subtraction of both images results in an optical section. The technique is also applicable to fluorescence imaging.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The invention claimed is:

1. A multimodal optical sectioning microscope for full-field imaging of a volumic and scattering sample comprising:
a full-field Optical Coherence Tomography (OCT) system for providing an image of a first section in depth of the sample comprising a first illumination sub-system and a full-field imaging interferometer, wherein the full-field imaging interferometer comprises:
a first beamsplitter for defining a reference arm and an object arm for receiving the sample, wherein the reference arm comprises a reference mirror and the object arm comprises a microscope objective,
a detection sub system, and
an optical conjugation device for optically conjugating the sample and said detection sub system, wherein said optical conjugation device comprises the microscope objective;
a supplementary full-field optical sectioning imaging system for providing a fluorescent image of a second section in depth of said sample comprising a structured illumination microscope, wherein the structured illumination microscope comprises:
a second illumination sub system separate from the first illumination sub system,
an imaging channel comprises the microscope objective of the full-field imaging interferometer and means for generating at the focal plane of said microscope objective a variable spatial pattern illumination, wherein the imaging channel is optically coupled with the object arm of the full-field imaging interferometer using the first beamplitter, and
a detection sub system, optically conjugated with said focal plane of the microscope objective; and
a second dichroic beamsplitter, wherein light emitted by the first and second illumination sub systems is combined in the object arm using the first beamsplitter and the second dichroic beamsplitter.

2. The multimodal optical sectioning microscope according to claim 1, wherein the supplementary full-field optical sectioning imaging system and the full-field OCT system have the same detection sub-system.

3. The multimodal optical sectioning microscope according to claim 1, wherein the supplementary full-field optical sectioning imaging system and the full-field OCT system have two separate detection sub-systems, and wherein the multimodal optical sectioning microscope further comprises a dichroic beamsplitter able to separate light retro diffused by said first section and fluorescent light emitted by said second section.

4. The multimodal optical sectioning microscope according to claim 1, wherein said means for generating the spatial pattern comprises a mask with variable spatial transmittance or reflectance to be illuminated by the illumination sub-system of said supplementary full-field optical sectioning imaging system and conjugated with the focal plane of said microscope objective.

5. The multimodal optical sectioning microscope according to claim 1, wherein the second illumination sub-system of said supplementary full-field optical sectioning imaging system is a laser, and said means for generating the spatial pattern comprises a diffuser to be illuminated by said laser and conjugated with the back aperture of said microscope objective.

6. A method for acquiring in depth section images of a first section of a volumic and scattering sample using a Full-Field Optical Coherence Tomography (FF-OCT) system comprising a full-field imaging interferometer and in depth section fluorescent images of a second section of said sample using a supplementary full-field optical sectioning imaging system comprising a structured illumination microscope, the method comprising:
acquiring the images of said first section of the sample by:
emitting light using a first illumination sub system, defining, in the full-field imaging interferometer, using a first beamsplitter, a reference arm and an object arm for receiving the sample, wherein said reference arm comprises a reference mirror and said object arm comprises a microscope objective, optically conjugating said sample with a detection sub-system of the full-field imaging interferometer using the microscope objective; and acquiring fluorescence images of said second section of the sample by:

emitting light using a second illumination sub-system, separate from the first illumination sub-system, wherein the light emitted by said first and second illumination sub-systems is combined in the object arm of the full-field imaging interferometer using a second dichroic beamsplitter and said first beamsplitter, optically coupling using said first beamsplitter an imaging channel of said structured illumination microscope with the object arm of the full-field imaging interferometer, wherein said imaging channel comprises said microscope objective and means for generating at the focal plane of said microscope objective a variable spatial pattern illumination, generating at the focal plane of said microscope objective of said full-field imaging interferometer a variable spatial pattern illumination, forming a plurality of images for different spatial pattern illumination on a detection sub-system optically conjugated with the focal plane of said microscope objective, and processing said plurality of images to obtain said fluorescence images.

7. A method according to claim 6, further comprising simultaneous acquisition of images from said supplementary full-field optical sectioning imaging system and said FF-OCT system.

8. A method according to claim 7, wherein simultaneous acquisition is obtained using spectral separation of light retro diffused by said first section and fluorescent light emitted by said second section.

9. A method according to claim 7, wherein simultaneous acquisition is obtained using a multispectral array detector common for said supplementary full-field optical sectioning imaging system and said FF-OCT system.

10. A method according to claim 7, wherein simultaneous acquisition is obtained using a single detection sub-system and the discrimination of data coming from said supplementary full-field optical sectioning imaging system, and wherein said FF-OCT system is performed using post processing of data acquired by said detection sub-system.

11. A method according to claim 6, further comprising displaying said first and second fluorescent images, and displaying merged images from said first and second fluorescent images.

12. A method according to claim 6, wherein acquiring images of said first section of the sample using the FF-OCT system further comprises acquiring using said imaging interferometer at least a first and a second interferometric images and processing said interferometric images to obtain said in depth section image of said first section.

* * * * *